United States Patent [19]
Peschl

[11] 3,939,701
[45] Feb. 24, 1976

[54] METHOD AND DEVICE FOR MEASURING THE SHEARING STRESS OF POWDERY AND/OR GRANULAR MATERIAL

[76] Inventor: Ivan Anton Slavko Zdravko Peschl, Kennedylaan 8, Sterksel, Netherlands

[22] Filed: Sept. 11, 1974

[21] Appl. No.: 504,906

[30] Foreign Application Priority Data
Sept. 14, 1973 Netherlands................ 7312665

[52] U.S. Cl. .............................................. 73/101
[51] Int. Cl.² ......................................... G01N 3/24
[58] Field of Search............................... 73/101, 99

[56] References Cited
UNITED STATES PATENTS
1,327,838  1/1920  Naylor ................................ 73/99

FOREIGN PATENTS OR APPLICATIONS
151,081  9/1962  U.S.S.R................................ 73/101

Primary Examiner—James J. Gill
Assistant Examiner—Anthony V. Ciarlante
Attorney, Agent, or Firm—Silverman & Cass, Ltd.

[57] ABSTRACT

Method of measuring shearing stress of powdery and-/or granular material using a pair of cylindrical cavities filled with the material. The cavities are turned one relative the other about a common center line with the shear stress required to turn the cavities being measured.

9 Claims, 2 Drawing Figures

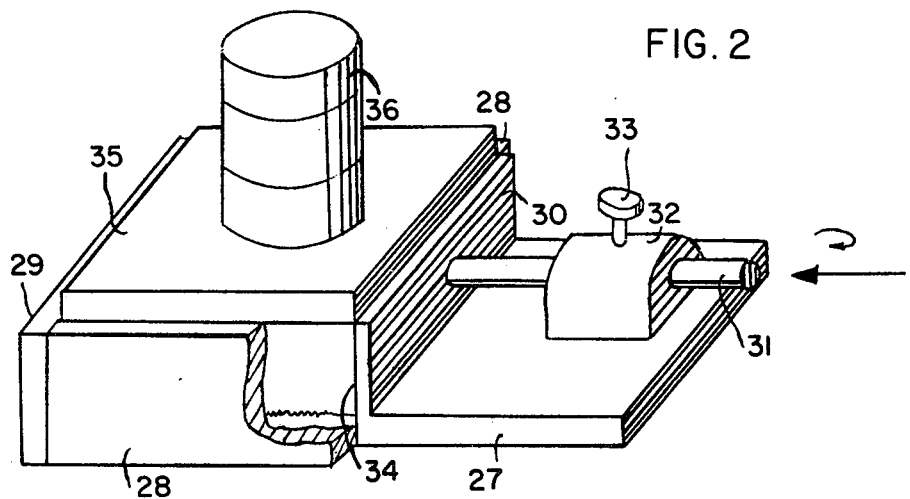

METHOD AND DEVICE FOR MEASURING THE SHEARING STRESS OF POWDERY AND/OR GRANULAR MATERIAL

The invention relates to a method of measuring the shearing stress in powdery and/or granular material, in which a sample is inserted into two relatively slidable members enclosing cavities of equal diameters.

In a known method of the kind set forth the two cavities are displaced relatively to the plane of separation between the two cavities and relative to one another, the force required for shearing being measured, and the shearing stress being determined on the basis of said force.

This method has the disadvantage that during the consolidation of the sample the main stress then occurring in the material exhibits a direction and value differing from those of the main stress during shearing. Consequently the state of stress during measurement is not unambiguously determined. Moreover, during measurement the surface of the sample and the shearing surface will vary so that only a small deflection is admissible.

The invention has for its object to provide a method of the kind set forth, in which the disadvantages of the prior method can be avoided in a simple and effective manner.

According to the invention this can be achieved by turning the members, whose cavities have a circular section, about a common centre line of the cavities relatively to one another for assessing the shearing stress.

A particularly efficient device for carrying out the method embodying the invention is obtained by providing it with a bottom plate, a member having a cylindrical cavity secured to said bottom plate and a second member bearing on the former member and having a cylindrical cavity coaxial to the cylindrical cavity of the first-mentioned member and with a lid adapted to be displaced in the direction of said common centre line of the cavities and to be turned about said centre line.

According to a further aspect the invention relates to a device for measuring the compression resistance of granular and/or powdery material.

According to the invention this device is provided with a bottom plate having two supports adapted to move relatively to one another along the bottom plate, between which a sample of granular and/or powdery material can be collected, the surface of the bottom plate located between the supports being partly roughened, which roughened portion extends from the support which is stationary to the bottom plate to an area slightly spaced apart from the initial position of the movable support.

When such a cell is employed, a sample of comparatively small height may be used, so that the material's own weight over the plane of fraction formed during the determination of the compression resistance is smaller than in known devices, whilst in addition the place of the plane of fracture is determined by the beginning of the roughened bottom portion.

The invention will now be described more fully with reference to embodiments of devices in accordance with the invention, illustrated in the accompanying drawings.

FIG. 2 is a perspective view of a device for measuring the compression resistance of granular and/or powdery material.

Figure 1:
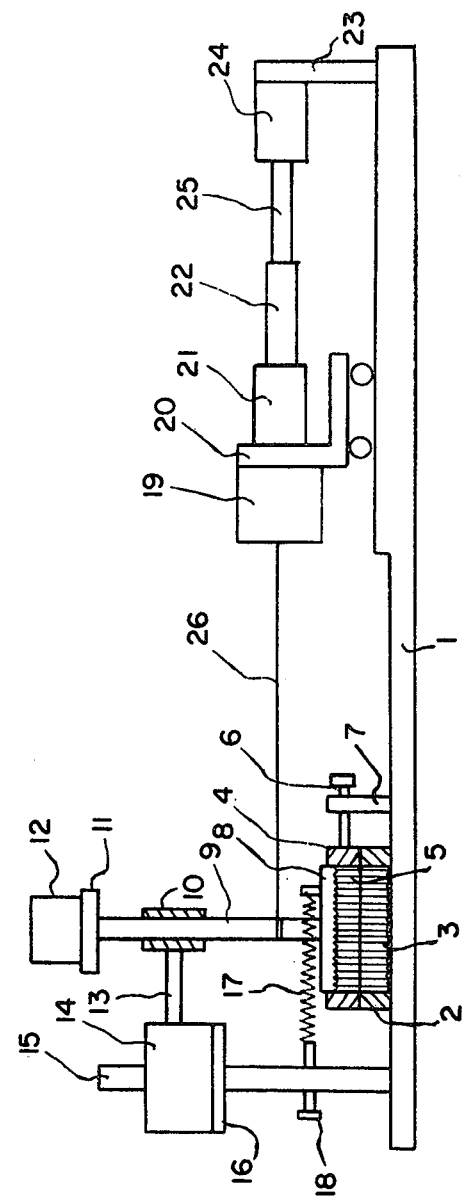
FIG. 1 is partly a schematic sectional view and partly an elevation of a device for measuring the shearing stress in powdery and/or granular material.

The device shown in FIG. 1 comprises a bottom plate 1, to which a cell 2 is secured, which encloses a cylindrical hollow space 3. The cell 2 holds a ring 4 enclosing a cylindrical hollow space 5. By means of a few setting bolts 6, screwed into supports secured to the bottom plate 1, only one of which is shown in the Figure, the ring 4 can be centered with respect to the cell 2 so that the centre lines of the cylindrical cavities 3 and 5 coincide, the parts being fixed in this position.

In the position shown in the Figure the upper part of the ring 4 holds a circular lid 8, secured to the lower end of a vertical shaft 9. The shaft 9 is journalled in a bearing 10 so as to be longitudinally slidable and a platform 11 is secured to the top end of the shaft 9 for receiving a weight 12.

By means of an arm 13 the bearing 10 is secured to a support 14, which is adapted to turn about a vertical shaft 15, secured to the bottom plate 1. The support 14 bears on a ring 16, secured to the shaft 15. To the top side of the lid 8, at a given distance from the centre line of the shaft 9, is secured one end of a tensile spring 17, the other end of which is connected with a set screw 18.

It is furthermore apparent from the Figure that the bottom side of the lid 8 is milled, whilst the portion of the bottom plate 1 enclosed by the cell 2 is preferably also milled. The inner walls of the cell 2 and of the ring 4, enclosing the cylindrical cavities 3 and 5 preferably have vertical grooves as shown.

A traction force meter 19 is secured to a slide 20 adapted to move along the bottom plate 1. To the slide 20 is fastened an electric motor 21, which is adapted to drive a hollow, tapped tube 22. To a support 23 rigidly secured to the bottom plate 1 is fastened an electric motor 24, which is adapted to drive a screwthreaded bar 25, screwed into the hollow tube 22.

The electric motor 21 is a slow-speed electric motor, whereas the electric motor 24 is a high-speed electric motor. In accordance with the electric motor put into operation the slide 20 with the tractive force meter 19 secured thereto will move slowly or rapidly.

The tractive force meter may have secured to it a cable 26, the other end of which may be wound a few times around the shaft 9.

The use and the operation of the device described above are as follows:

In order to assess the shearing stress of a powdery and/or granular material the cylindrical cavities 3 and 5 enclosed by the cell 2 and the ring 4 respectively are filled with said material, after the ring is fixed in the correct position relative to the cell 2 by means of the set bolts 6 so that the centre lines of the cylindrical cavities 3 and 5 coincide. This can be achieved by turning the support 14 with the lid 8 about the centre line of the shaft 15 so that the lid 8 is located at the side of the ring 4.

Then the lid 8 is returned to the position shown in the Figure, after which the material is consolidated in the cavities 3 and 5 by putting a weight 12 on the lid 8.

At the same time such a force is generated in the spring 17 that the material is subjected to a coupling force which is at least substantially equal to the final uncoupling force occurring in shearing. This is achieved by stretching the spring until the lid 8 slightly shifts in place. During consolidation this operation may be repeated.

In order to measure the shearing stress subsequent to consolidation of the material the spring 17 is relaxed, the cable 26 is connected with the shaft 9 and the set bolts 6 are unscrewed for releasing the ring 4. Subsequently, by means of the slow-speed electric motor the slide 20 with the traction force meter 19 is displaced so that by means of the cable 26 the shaft 9 and hence the lid 8 and the ring 4 are turned about the centre line of the shaft 9, the material being thus shifted in the interface between the cell 2 and the ring 4. The force required for this shearing effect can be assessed by means of the meter 19.

The various rotational and translatory movements may be performed practically without friction, provided air bearings or the like are employed.

In this way a simple measuring device is obtained, which provides several advantages. The preparation of the samples can be simply and rapidly. The state of stress during the consolidation of the material corresponds with that during shearing, whilst as a result of the rotary movement and the central position of the ring 4 maintained with respect to the cell the surfaces of the sample and of the shearing surface remain constant so that the measuring results will be more accurate. Owing to the rotary movement the deflection is not limited so that several measurements can be carried out on the same sample.

The measurements may be carried out in a conventional manner with different loads and on the basis of the measuring results further data may be assessed, for example, inner angle of friction, cohesion, resistance to compression, outer angle of friction and yield point.

The device shown in FIG. 2 is particularly suitable for messuring the compression resistance of granular and/or powdery material.

This cell comprises a bottom plate 27, to which are secured in a readily detachable manner sidewalls 28 and a rear wall 29 for example by means of bolts.

A stamp 30 is provided, to which a rod 31 is secured. The rod 31 is taken through a bearing 32 secured to the bottom plate and can be fixed in it in any desired position by means of a clamp screw 33.

The bottom portion located between the rear wall 29 and the stamp 30 is partly milled and the boundary line 34 of the milled portion extends parallel to the stamp 30.

The space enclosed by the sidewalls 28, the rear wall 29 and the stamp 30 can receive a sample of a granular and/or powdery material. The space is then covered by a fitting lid 35, on which weights 36 can be put down for consolidating the sample. During this operation the rod 31 is clamped tight with the aid of the clamp screw 33. After consolidation the weights 36 and the lid 35 are removed and the clamp screw 33 is loosened whilst at the same time a slight force is exerted in the direction of the arrow P on the rod 31 in order to prevent the stamp from moving away from the sample.

Subsequently the force P exerted on the sample is increased until the sample breaks down. This force divided by the surface of the stamp is the compression resistance of the sample.

The bottom is milled for preventing a shift in place of the sample along the bottom, whilst the bottom portion located near the stamp is smooth over a small distance in order to minimize the resistance during depression and displacement of the sample.

When the device described above is employed, the height of the sample may be comparatively small so that the natural weight of the material above the plane of fracture is also small. Moreover, the place of the plane of fracture is accurately defined by the beginning of the milled bottom.

The sidewalls 28 may remain in the position shown during the assessment of the compression resistance, which is particularly important for measurements on materials of very weak cohesion.

What we claim is:

1. Method for measuring the shearing stress of powdery and/or granular material with a pair of members displaceable relative to each other about a common intersection therebetween, the members being of circular cross-section with equal diameters and enclosing hollow cavities therebetween, the cavities having a common center line, said method comprising the steps of:

A. filling the cavities completely with a sample of the material,
    B. placing a freely movable weight on the material in the members,
    C. turning the completely filled members with respect to each other about the center line of the cavities by rotating the weight to shear the material at the intersection between the members, and
    D. measuring the force required to shear the material.

2. Method as claimed in claim 1 including the step of exerting a force on one of the members during the step of filling, said force being at least substantially equal to the force required to turn the members during the step of turning.

3. Method as claimed in claim 1 in which there is a first member defining a first cylindrical cavity and a second member resting on the first member and defining a second cylindrical cavity arranged coaxially with the first cavity, a lid freely displaceable in the direction of the common center line of the cavities and rotatable about said center line, the walls of the cavities being formed with vertically arranged grooves.

4. Method as claimed in claim 3 in which the lid is operatively connected to the weight by a vertical shaft disposed therebetween and said shaft is longitudinally displaceable in a bearing adapted to turn about a second shaft disposed parallel to said vertical shaft.

5. Method as claimed in claim 3 in which a spring is coupled at one end thereof to the lid at a distance from the center line of the lid, and the spring is connected at the other end thereof to an adjusting device.

6. Method as claimed in claim 3 in which the members are adapted to be aligned and fixed with respect to each other by set screws.

7. Method as claimed in claim 4 in which the step of measuring is performed with a traction meter, the meter being secured to a slide and connected to the vertical shaft by a cable, the slide being displaceable by a driving member.

8. Method as claimed in claim 7 in which a first electric motor is connected with the slide and a second electric motor is coupled to the first motor by a hollow tapped tube and a screwthread bar screwed therein, the tube being drivable by one of the motors and the bar being drivable by the other motor, one of the motors being a slow-speed motor and the other being a high-speed motor.

9. Method as claimed in claim 3 in which the bottom surface of the first cavity and the surface of the lid facing the sample are milled.

* * * * *